United States Patent [19]

Fuller

[11] Patent Number: 5,905,091
[45] Date of Patent: May 18, 1999

[54] ENHANCEMENT OF SKIN PIGMENTATION BY PROSTAGLANDINS

[75] Inventor: Bryan B. Fuller, Edmond, Okla.

[73] Assignee: The Board of Regents of The University of Oklahoma

[21] Appl. No.: 08/886,795

[22] Filed: Jul. 1, 1997

Related U.S. Application Data

[60] Provisional application No. 60/021,242, Jul. 3, 1996.

[51] Int. Cl.⁶ ............................... A61K 7/42; A61K 7/40
[52] U.S. Cl. ............................ 514/573; 424/59; 424/401
[58] Field of Search ............................ 514/573; 424/401, 424/59

[56] References Cited

U.S. PATENT DOCUMENTS

| | | | |
|---|---|---|---|
| 4,182,725 | 1/1980 | Voorhees et al. | 424/258 |
| 5,219,885 | 6/1993 | Frölich et al. | 514/530 |
| 5,554,359 | 9/1996 | Fuller | 424/59 |

FOREIGN PATENT DOCUMENTS

| | | |
|---|---|---|
| 0302147 | 2/1989 | European Pat. Off. . |
| 2235678 | 6/1974 | France . |
| 9517161 | 4/1995 | WIPO . |
| 9511003 | 6/1995 | WIPO . |

OTHER PUBLICATIONS

Bryan B. Fuller and Joyce Lebowitz, "Decay of Hormone Responsiveness in Mouse Melanoma Cells in Culture as a Function of Cell Density", *Journal of Cellular Physiology*, vol. 103, pp. 279–287, 1980.

Frank L. Meyskens, Jr., Elizabeth B. Bergludn, Debra F. Saxe, Bryan B. Fuller, Laura Z. Pacelli, Jennifer D. Hall, and C. George Ray, "Biological and Biochemical Properties of a Human Uveal Melanocyte–Derived Cell Line", *In Vitro*, vol. 16, No. 9, pp. 775–780, 1980.

Bryan B. Fuller and Frank L. Meyskins, "Endocrine Responsiveness in Human Melanocytes and Melanoma Cells in Culture", *JNCL*, vol. 66, No. 5, pp. 799–802, May 1981.

James J. Nordlund, Cynthia E. Collins, and Lawrence A. Rheins, "Prostaglandin $E_2$ and $D_2$ but Not MSH Stimulate the Proliferation of Pigment Cells in the Pinnal Epidermis of the DBA/2 Mouse", *J. Invest. Dermatol.*, vol. 86, pp. 433–437, 1986.

Alice P. Pentland and Philip Needleman, "Modulation of Keratinocyte Proliferation In Vitro by Endogenous Prostaglandin Synthesis", *J. Clin. Invest.*, vol. 77, Jan. 1986.

Yasushi Tomita, Masatoshi Iwamoto, Takayuki Masuda, and Hachiro Tagami, *J. Invest. Dermatol.*, vol. 89, pp. 299–301, 1987.

Phillip R. Gordon, Claire P. Mansur, and Barbara A. Gilchrest, "Regulation of Human Melanocyte Growth, Dendricity, and Mealnization by Keratinocyte Derived Factors", *J. Invest. Dermatol.*, vol. No. 92, pp. 565–572, 1989.

Mitsuru Iwata, Shoko Iwata, Mark A Everett, and Bryan B. Fuller, "Hormonal Stimulation of Tyrosinase Activity in Human Foreskin Organ Cultures", *In Vitro Cell. Dev. Biol.*, vol. 26, pp. 554–560, Jun. 1990.

"Xalatan" Drug Lasert, Pharmacia & Upjohn, Jun. 3, 1996.
Abdel et al., In Vitro Modulation of Proliferation and Melanization of S91 Melanoma Cells by Prostaglandins, *Cancer Research*, 3141–3146, Jun. 15, 1987.

*Primary Examiner*—Nathan M. Nutter
*Attorney, Agent, or Firm*—Dunlap, Codding, & Rogers, Inc.

[57] ABSTRACT

A composition comprising a carrier and prostaglandin effective in stimulating synthesis of melanin in a human melanocyte thereby enhancing pigmentation of the human skin and optionally comprising a lysosomotropic agent, a phosphodiesterase inhibitor, and/or methylxanthines, and a method of use of the composition. Use of this composition promotes tanning of the human skin and increases photoprotection from ultraviolet radiation.

29 Claims, 8 Drawing Sheets

ENHANCEMENT OF SKIN PIGMENTATION BY PROSTAGLANDINS

CROSS REFERENCE TO RELATED APPLICATIONS

This application claims the benefit of U.S. Provisional Application Ser. No. 60/021,242, filed Jul. 3, 1996.

BACKGROUND

The present invention generally relates to pigmentation enhancing compositions for topical application on a subject's skin, and specifically, to pigmentation enhancers comprising a prostaglandin.

Skin color in humans arises from a complex series of cellular processes which are carried out within a unique population of cells called melanocytes. Melanocytes are located in the lower part of the epidermis, and their function is to synthesize a brown pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the melanocytes. The melanosomes are extruded from the melanocytes and carried to the surface of the skin by keratinocytes, which internalize the melanin containing melanosomes. The end result is that the visible layers of the skin exhibit a brown color typically known as a "tan".

The darkness of the color observed in the skin is proportionate to the amount of melanin synthesized by melanocytes and transferred to the keratinocytes. By increasing natural melanogenesis, skin can be at least partially shielded from ultraviolet radiation, and tanning of the skin can be achieved without exposure of the skin to potentially damaging ultraviolet radiation.

SUMMARY OF THE INVENTION

The objective of the present invention is to provide a composition which can be topically applied to the skin to result in the delivery of a prostaglandin which is effective in enhancing melanogenesis in melanocytes into the skin for use as a method for inducing skin pigmentation (tanning).

The present invention comprises a composition of matter comprising an amount of at least one prostaglandin effective in increasing levels of melanin in a human melanocyte. The composition also comprises an effective amount of a pharmaceutically acceptable topical carrier which is capable of delivering the effective prostaglandin to the melanocyte under in vivo conditions.

The present invention also comprises a method for enhancing or promoting pigmentation (tanning) in the skin of a subject. The subject's skin is treated with a pigment enhancer comprising an effective prostaglandin and optionally a methylxanthine, a phosphodiesterase inhibitor, or a lysosomotropic agent effective in increasing the amount of melanin in a human melanocyte, and a pharmaceutically acceptable topical carrier as previously described. Such a method of application may further function to at least partially shield the subject's skin from ultraviolet radiation.

More particularly, the present invention contemplates a composition, and method of using such, which is effective in stimulating melanogenesis in human skin, the composition comprising an effective amount of a prostaglandin effective in increasing levels of melanin in melanocytes in human skin. More particularly, the invention contemplated herein is restricted to a class of prostaglandins wherein the prostaglandin or salt, derivative or analog thereof has a cyclopentane ring having positions 8–12, a side chain bonded to the 8 position in an α configuration, and a side chain bonded to the 12 position in a β configuration, and wherein the cyclopentane ring further comprises (1) a carbonyl oxygen in the 9 position, (2) an epidoxy group in the 9, 11 position, or (3) a first hydroxyl group bonded to the 9 position in a β configuration and a second hydroxyl group bonded to the 11 position in an α configuration.

DETAILED DESCRIPTION OF THE INVENTION

Figure 1:
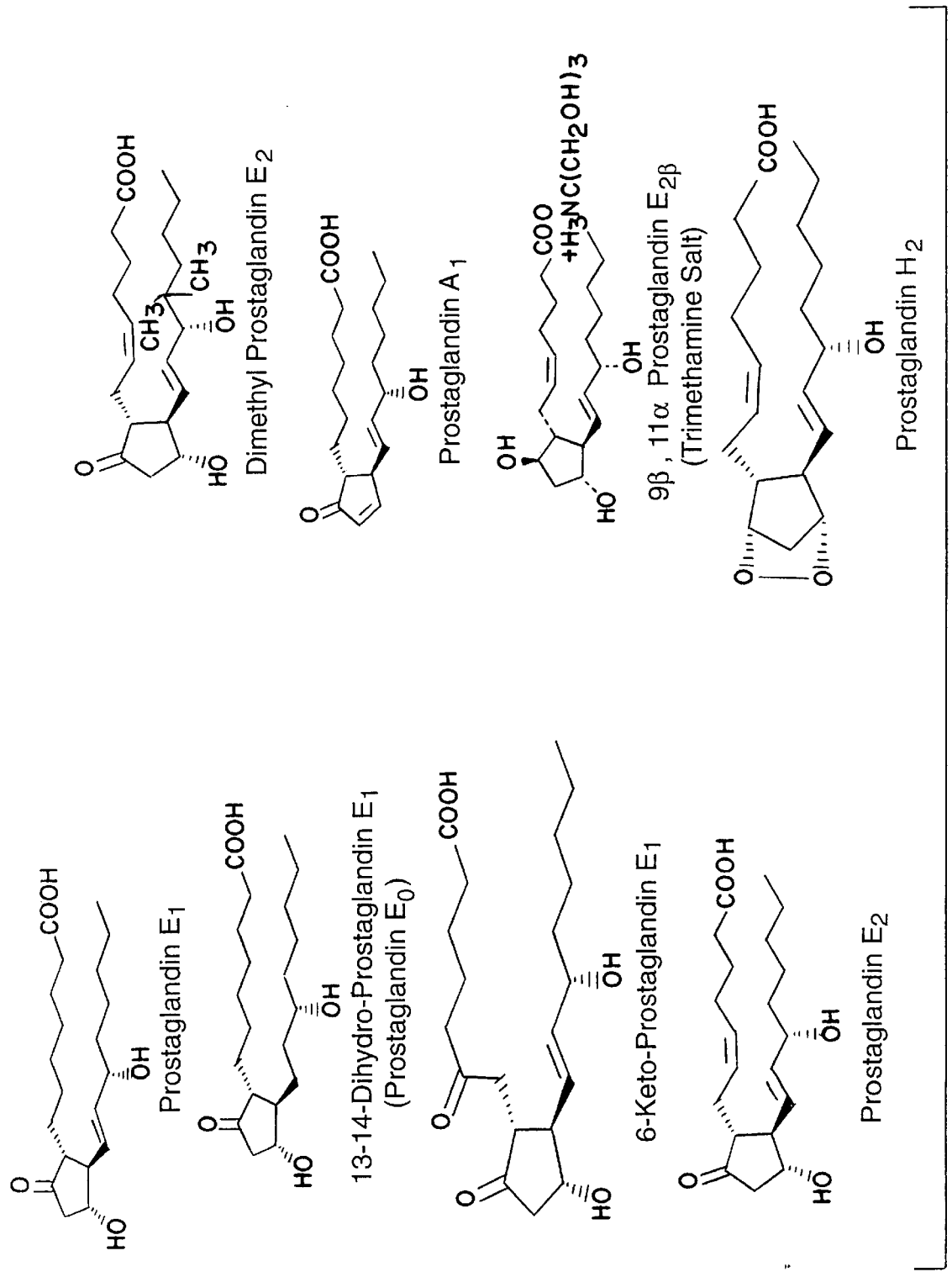
FIG. 1 shows general formulas of several of the prostaglandins claimed herein, the general formula showing an 8α, 12β side chain configuration.

The present invention is directed to compositions and methods which increase melanogenesis in subjects. "Subjects" as used herein mean mammals, and, more preferably, humans.

The present invention comprises compositions comprising an effective amount of one or more agents capable of increasing the amount of melanin in a melanocyte (also referred to herein as "melanin-increasing agents") and, more preferably, in a human melanocyte, and more preferably, in melanocytes in intact human skin. The melanin-increasing agent may function in any of the various ways that are believed to increase the amount of melanin: by increasing cAMP (cyclic AMP) or derivatives of cAMP which function as cAMP in the melanocyte; by inhibiting phosphodiesterase; or by increasing tyrosinase activity; or by other mechanisms not described herein. The melanin-increasing agent is capable, alone or with the aid of a carrier as described hereafter, of crossing the melanocyte membrane, or attaching to the membrane, and more preferably, a human melanocyte membrane, in order to function in a manner as will be described below.

It is Applicant's unique discovery, described further herein, that certain prostaglandins are effective in stimulating melanin production in melanocytes and therefore are effective in enhancing skin pigmentation. More particularly, the present invention contemplates a composition, and method of using such, which is effective in stimulating melanogenesis in human skin. The composition comprises an effective amount of a prostaglandin effective in increasing levels of melanin in a human melanocyte.

As contemplated herein, the invention is a composition for use in stimulating melanogenesis in human skin melanocytes, which comprises an effective amount of a prostaglandin or a salt, derivative or analog thereof which is able to increase levels of melanin in a human melanocyte, and an effective amount of a pharmaceutically acceptable carrier capable of delivering the effective amount of the prostaglandin to the melanocyte in the skin.

More particularly, the invention contemplated herein is restricted to a class of prostaglandins wherein the prostaglandin or salt, derivative or analog thereof has a cyclopentane ring having positions 8–12, a side chain bonded to the 8 position in an α configuration, and a side chain bonded to the 12 position in a β configuration, and wherein the cyclopentane ring further comprises (1) a carbonyl oxygen in the 9 position, (2) an epidoxy group in the 9, 11 position, or (3) a first hydroxyl group bonded to the 9 position in a β configuration and a second hydroxyl group bonded to the 11 position in an α configuration.

The prostaglandin preferably has the general formula I:

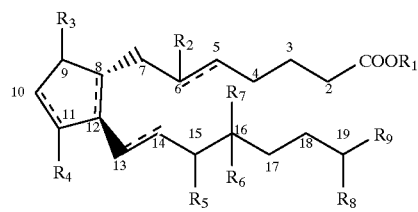

(I)

in which $R_1$ is a hydrogen atom, an alkyl residue, a sulfonyl residue or a derivative thereof, or a tromethamine group, $R_2$ is a hydrogen atom, or a carbonyl oxygen atom when the $C_5$–$C_6$ bond is single or is absent when the $C_5$–$C_6$ bond is double, $R_3$ is a carbonyl oxygen atom, an oxygen atom bonded to another oxygen atom in the 11 position, or a β-hydroxyl group, $R_4$ is a hydrogen or hydroxyl group when the $C_{10}$–$C_{11}$ bond is a single bond, is absent when the $C_{10}$–$C_{11}$ bond is a double bond, is an oxygen atom bonded to an oxygen atom in the 9 position, or is an α-hydroxyl group when $R_3$ is a β-hydroxyl group, $R_5$ is a hydrogen atom, a hydroxyl group, a carbonyl oxygen, or a hydroxyl and methyl pair, $R_6$ is a hydrogen atom or a methyl group, $R_7$ is a hydrogen atom or a methyl group, $R_8$ is a hydrogen atom or a hydroxyl group, and $R_9$ is a hydroxyl group or an alkyl residue.

The composition further comprises an effective amount of a pharmaceutically acceptable topical carrier capable of delivering the prostaglandin to the melanocyte in the skin. Where used in the formula, a dashed line adjacent a solid line between two carbon atoms is meant to indicate that the bond between the two carbon atoms may be a single bond or a double bond.

Prostaglandins which are effective in the present invention include:

$PGA_1$; $PGA_2$; $PGB_2$; $PGE_1$; $PGE_2$; $PGH_2$; 6-keto $PGE_1$; 13,14-dihydro $PGE_1$; Misoprostol; 11-deoxy $PGE_1$; 8-iso $PGE_1$; 11-β $PGE_1$; 15(R)-$PGE_1$; 15-keto $PGE_1$; 13,14-dihydro-15(R) $PGE_1$; 13,14-dihydro-15-keto $PGE_1$; 16,16-dimethyl-6-keto $PGE_1$; 19(R)-hydroxy $PGE_1$; 16,16-dimethyl $PGA_1$; 13,14-dihydro-15-keto $PGA_2$; 16,16-dimethyl $PGA_2$; 17-phenyl trinor-13,14-dihydro $PGA_2$; 8-iso $PGE_2$; 15-keto $PGE_2$; 16,16-dimethyl $PGE_2$; 11β-$PGE_2$; 13,14-dihydro-15-keto $PGE_2$; 15(R)-$PGE_2$; $PGE_2$ methyl ester; Sulprostone; 17-phenyl trinor $PGE_2$; 19(R)-hydroxy $PGE_2$; 20-hydroxy $PGE_2$; $PGF_{1\beta}$; $PGF_{2\beta}$ (also known as 9β,11αPGF$_{2\beta}$); 5-trans PGF$_{2\beta}$; and tromethamine salts of the above, e.g., 9β,11αPGF$_{2\beta}$ tromethamine). Prostaglandins such as those listed herein are commercially available from such sources as Cayman Chemical Co and Biomol Research Laboratories. Standard names of these prostaglandins are shown in Tables I and II.

Prostaglandins which have been determined to be ineffective or have a low effectiveness in stimulating melanogenesis in melanocytes include: $PGB_1$; $PGD_2$; $PGF_{1\alpha}$; $PGF_{2\alpha}$; 15-keto $PGF_{2\alpha}$; 6-keto $PGF_{1\alpha}$; Latanoprost; 6,15-diketo-13,14-dihydro $PGF_{1\alpha}$; 8-iso $PGF_{1\beta}$; 8-iso $PGF_{2\beta}$; 11β-$PGF_{1\beta}$; 11β-$PGF_{2\alpha}$; and $PGJ_2$.

Preferably the effective prostaglandin has a keto group (a carbonyl oxygen) in the 9 position of the cyclopentane ring. Examples of such prostaglandins are prostaglandin $E_1$, prostaglandin $E_2$, 16,16-dimethyl prostaglandin $E_2$, 6-keto prostaglandin $E_1$, 13,14-dihydro prostaglandin $E_1$, prostaglandin $A_1$, and prostaglandin $A_2$, the general formulas of which are represented in FIG. 1.

Prostaglandin $B_1$ although having a 9 position keto group is not adequately effective. In contrast, prostaglandins $A_1$ and $A_2$ have a double bond between $C_{10}$ and $C_{11}$, and while not exhibiting as high a degree of effectiveness as 9-keto prostaglandins with saturated cyclopentane rings, do exhibit an intermediate level of activity.

Prostaglandin $H_2$, also represented by a formula shown in FIG. 1, is also effective in accordance with the present invention. And may comprise the prostaglandin of the present invention. In prostaglandin $H_2$, and similar prostaglandins, the $R_3$ group and $R_4$ group of Formula I comprise oxygen atoms having a single bond at the 9 and 11 positions respectively, and are bonded via a single bond between the two oxygen atoms, forming an epidoxy group and thereby comprise an alternative version of the invention.

In yet another alternative of the invention, the effective prostaglandin comprises an F prostaglandin having a 9β hydroxyl and an 11α hydroxyl (wherein the first side chain is bonded in the α configuration to the cyclopentane and the second side chain is bonded in the β configuration to the cyclopentane. Examples of such prostaglandins are $PGF_{1\beta}$, 5-trans $PGE_{2\beta}$ and 9β,11αPGF$_{2\beta}$ and its tromethamine salt (shown in FIG. 1). Prostaglandins which do not show significant melanogenic activity and thus are not considered within the scope of the present invention are those having (1) 9α,11α hydroxyl groups; (2) 9β,11β hydroxyl groups; (3) 9α,11β hydroxyls (e.g., 11β-$PGF_{2\alpha}$); and (4) 9β,11α hydroxyls, with both side chains in a β projection (e.g. latanoprost, $PGF_{1\alpha}$, $PGF_{2\alpha}$, 8-iso $PGF_{1\beta}$, 8-iso $PGF_{2\beta}$, 6-keto $F_{1\alpha}$, 15-keto $F_{2\alpha}$, and 6,15-diketo,13,14 dihydro $F_{1\alpha}$). In order for an F prostaglandin to be considered effective, then, it must have the two side chains in the normal α,β prostanoic acid configuration and have the hydroxyl groups in the 9β, 11α positions.

The prostaglandin may comprise from about 0.01 μM to about 10 mM of the composition, or from about $10^{-4}$% to about 1% by weight of the composition. More preferably, the prostaglandin comprises from about $10^{-4}$% to about 0.1% by weight of the composition. More preferably, the prostaglandin comprises from about $10^{-3}$% to about 0.1% by weight of the composition.

TABLE I
EFFECTIVE PROSTAGLANDINS

| Prostaglandin Name | Chemical Notation |
|---|---|
| PGA$_1$ | Prosta-10,13-dien-1-oic acid, 15-hydroxy-9-oxo-,(13E,15S)- |
| PGA$_2$ | Prosta-5,10,13-trien-1-oic-3,3,4,4-d$_4$ acid, 15-hydroxy-9-oxo-,(5Z,13E,15S)- |
| PGB$_2$ | Prosta-5,8(12),13-trien-1-oic acid, 15-hydroxy-9-oxo-,(5Z,13E,15S)- |
| PGE$_1$ | Prost-5,13,17-trien-1-oic acid, 9,15,-dihydroxy-11-oxo-,(5Z,9α,13E,15S,17Z)- |
| PGE$_2$ | Prosta-5,13-dien-1-oic-acid, 11,15-dihydroxy-9-oxo-,(5Z,11α,13E,15S)- |
| PGH$_2$ | Prosta-5,13-dien-1-oic acid, 9,11-epidoxy-15-hydroxy-,(5Z,9α,13E,15S)- |
| 6-keto PGE$_1$ | Prost-13-2n-1-oic acid, 11,15-dihydroxy-6,9-dioxo,(11α,13E,15S)- |
| 13,14-dihydro PGE$_1$ | Prostan-1-oic acid, 11,15-dihydroxy-9-oxo-,(11α,15S)- |
| Misoprostol | Prost-13-2n-oic acid, 11,16-dihydroxy-16-methyl-9-oxo, methyl ester,(11α,13E)- |
| 11-deoxy PGE$_1$ | Prost-13-en-1-oic acid, 15-hydroxy-9-oxo-,(13E,15S)- |
| 8-iso PGE$_1$ | Prost-13-en-1-oic acid, 11,15-dihydroxy-9-oxo-,(8β,11α,13E,15S)- |
| 11-β PGE$_1$ | Prost-13-en-1-oic acid, 11,15-dihydroxy-9-oxo,(11β,13E,15S)- |
| 15-R PGE$_1$ | Prost-13-2n-1-oic acid, 11,15-dihydroxy-9-oxo-,(11α,13E,15R)- |
| 15-keto PGE$_1$ | Prost-13-en-1-oic acid, 11-hydroxy-9,15-dioxo-,(11α,13E)- |
| 13,14-dihydro-15-R PGE$_1$ | Prostan-1-oic acid, 11,15-dihydroxy-9-oxo,(11α,15R)- |
| 13,14-dihydro-15-keto PGE$_1$ | Prostan-1-oic acid, 11-hydroxy-9,15-dioxo-,(11α)- |
| 16,16-dimethyl 6 keto PGE$_1$ | Prost-13-en-1-oic acid, 11,15,19-trihydroxy-9-oxo-,(11α,13E,15S,19R)- |
| 19(R) hydroxy PGE$_1$ | Prost-13-en-1-oic acid, 11,15,19-trihydroxy-9-oxo,(11α,13E,15S,19R)- |
| 16,16-dimethyl PGA$_1$ | Prosta-10,13-dien-1-oic acid, 15-hydroxy-16,16-dimethyl-9-oxo-,(13E,15R)- |

TABLE II
EFFECTIVE PROSTAGLANDINS CONT . . .

| Prostaglandin Name | Chemical Notation |
|---|---|
| 13,14-dihydro-15-keto PGA$_2$ | Prosta-5,10,13-trien-1-oic-3,3,4,4-d$_4$ acid, 15-hydroxy-9-oxo,(5Z,13E,15S)- |
| 16,16-dimethyl A$_2$ | Prosta-5,10,13,trien-1-oic acid, 15-hydroxy-16,16-dimethyl-9-oxo-,(5Z,13E,15R)- |
| 17-phenyl trinor-13,14-dihydro PGA$_2$ | 5-Heptenoic acid, 7-[2-(3-hydroxy-5-phenylpentyl)-5-oxo-3-cyclopenten-1-yl]-,[1R-[1α(Z),2β(R*)]]- |
| 8-iso PGE$_2$ | Prosta-5,13,dien-1-oic acid, 11,15-dihydroxy-9-oxo-,(5Z,8β,11α,13E,15S)- |
| 15-keto PGE$_2$ | Prosta-5,13-dien-1-oic acid, 11-hydroxy-9,15-dioxo-,(5Z,11α,13E)- |
| 16,16-dimethyl PGE$_2$ | Prosta-5,13-dien-1-oic acid, 11,15-dihydroxy-16,16-dimethyl-9-oxo,(5Z,11α,13E,15R)- |
| 11β PGE$_2$ | Prosta-5,13-dien-1-oic acid, 11,15-dihydroxy-9-oxo-,(5Z,11β,13E,15S)- |
| 13,14-dihydro-15-keto PGE$_2$ | Prost-5-en-1-oic acid, 11-hydroxy-9,15-dioxo-,(5Z,11α)- |
| 15-(R) PGE$_2$ | Prosta-5,13-dien-1-oic acid, 11,15-dihydroxy-9-oxo-,(5Z,11α,13E,15R)- |
| PGE$_2$ methyl ester | Prosta-5,13-dien-1-oic acid, 11,15-dihydroxy-9-oxo-, methyl ester,(5Z,11α,13E,15S)- |
| Sulprostone | 5-Heptenamide,7-[3-hydroxy-2-(3-hydroxy-4-phenoxy-1-butenyl)-5-oxocyclopentyl]-N-(methylsulfonyl)-,[1R-[1α(Z),2β(1E,3R*),3α]]- |
| 17-phenyl trinor | 5-Heptenoic acid, 7-[3-hydroxy-2-(3-hydroxy-5- |

TABLE II-continued
EFFECTIVE PROSTAGLANDINS CONT . . .

| Prostaglandin Name | Chemical Notation |
|---|---|
| PGE$_2$ | phenyl-1-pentenyl)-5-oxocyclopentyl]-,[1R-[1α(Z),2β(1E,3S*),3α]]- |
| 19(R)-hydroxy PGE$_2$ | Prosta-5,13-dien-1-oic acid, 11,15,19-trihydroxy-9-oxo-,(5Z,11α,13E,15S,19R)- |
| 20-hydroxy PGE$_2$ | Prosta-5,13-dien-1-oic acid, 11,15,20-trihydroxy-9-oxo-,(5Z,11α,13E,15S)- |
| PGF$_{1β}$ | Prost-13-2n-1-oic acid, 9,11,15-trihydroxy-,(9β,11α,13E,15S)- |
| PGF$_{2β}$ | Prosta-5,13-dien-1-oic acid, 9,11,15-trihydroxy-,(5Z,9β,11α,13E,15S)- |
| 5-trans PGF$_{2β}$ | Prosta-5,13-dien-1-oic acid, 9,11,15-trihydroxy-(5E,9β,11α,13E,15S)- |
| PGF$_{2β}$, (tromethamine salt) | Prosta-5,13-dien-1-oic acid, 9,11,15-trihydroxy-(5Z,9β,11α,13E,15S)-, compd. with 2-amino-2-(hydroxymethyl)-1,3-propanediol(1:1) |

The composition may further comprise a methylxanthine selected from the group consisting of theophylline, isobutyl methylxanthine, aminophylline and analogs, derivatives, isomers and pharmaceutically acceptable salts of theophylline, isobutyl methylxanthine or aminophylline capable of increasing melanin in the human melanocyte and wherein the pharmaceutically acceptable topical carrier is capable of delivering the methylxanthine to the melanocyte under in vivo conditions. In such a composition the methylxanthine preferably has a concentration of from about 0.01 mM to about 100 mM in the composition. Further, the composition may comprise an effective amount of dibutyryl cAMP. Also, the composition may further comprise a lysosomotropic agent.

The prostaglandins used herein may be obtained from natural sources such as algae (e.g. *Gracillaria verrucosa*) and gorgonian coral using methods of extraction known to those of ordinary skill in the art.

As noted above, the melanin-increasing agent of the present invention preferably comprises at least a 9-keto prostaglandin, or a 9,11 epidoxy prostaglandin, or a 9β,11α dihydroxy F prostaglandin and, optionally a phosphodiesterase-inhibitor, a methylxanthine, or a lysosomotropic agent. Phosphodiesterase-inhibitors are believed to increase the amount of cAMP in biological systems. Cyclic-AMP is believed to increase the activity of tyrosinase, which is the rate limiting enzyme which transforms the substrate tyrosine into melanin. When the composition comprises a methylxanthine, it is preferably a methylxanthine capable of functioning as a phosphodiesterase inhibitor. Most preferably, the additional agent comprises theophylline, isobutyl methylxanthine (IBMX), or a derivative thereof such as aminophylline or effective salts thereof. Examples of salts and derivatives of theophylline which may be used in the present invention are aminophylline, theophylline calcium salicylate, theophylline sodium salicylate, sodium theophylline, theophylline ethanolamine, theophylline diethanolamine, theophylline isopropanolamine, theophylline sodium acetate, and theophylline sodium glycinate. The melanin-increasing agent may also comprise any pharmaceutically acceptable salt, analog, derivative or isomer of any prostaglandin, phosphodiesterase inhibitor, methylxanthine or lysosomotropic agent capable of functioning as described herein.

A lysosomotropic agent is defined herein as a compound which enters a cell, accumulates in lysosomes, and causes a decrease in the lysosome transmembrane proton gradient, thereby increasing the pH inside the organelle. Lysomotropic agents are known to increase the internal pH of acidic vesicles and include the compounds ammonium chloride, monensin, nigericin, methylamine and ethylamine. The addition of such compounds may activate preexisting but catalytically inactive tyrosinase in melanosomes.

The melanin-increasing agent is present in the compositions of the present invention in any effective amount. An "effective amount" of the melanin-increasing agent is an amount which increases melanogenesis in the treated area of the subject. This amount may vary with, among other things, the identity of melanin-increasing agent and carrier, the subject's skin color and condition, and the degree of tanning and/or photoprotection sought.

This increased melanin would provide a tan without exposure to the sun, and by virtue of its UV absorbing properties, would also provide increased photoprotection from solar radiation. Fair-skinned individuals who tan poorly and are thus at high risk for developing sun-induced skin cancer, would greatly benefit. The increased tan induced by the effective prostaglandin compounds described herein or other melanogenic compounds will help reduce the risk of skin cancer in these individuals.

As previously discussed, the enzyme tyrosinase converts the substrate tyrosine into melanin. Since the composition of the present invention is believed to increase tyrosinase activity, the present invention optionally further comprises an effective amount of tyrosine so that the tyrosinase has as much substrate as possible to synthesize melanin. An "effective amount" of tyrosine means any amount which can be utilized by tyrosinase over the amount of tyrosine already present in the melanocyte. Preferably, the tyrosine comprises a concentration of from about 0.01 mM to about 1 mM of the composition of the present invention.

The composition of matter of the present invention is preferably applied directly to the skin of the individual seeking tanning of the skin and/or photoprotection from ultraviolet radiation. The treated area can be the entire skin surface of the subject or only those areas normally exposed to ultraviolet radiation. Application of the composition may be repeated periodically for greater protection and/or tanning effect.

As noted above, the compositions of matter of the present invention additionally comprises an effective amount of a pharmaceutically acceptable topical carrier capable of delivering the agent to the melanocyte under in vivo conditions. The carrier may comprise any solution, suspension, emulsion or any other form which is capable of delivering the agent to the melanocyte under in vivo conditions. "Capable of delivery", as used herein, means that the carrier should permit the agent to cross the stratum corneum and successive cell layers found epidermal to the melanocyte, and/or aids the agent in crossing the melanocyte membrane. Furthermore, the carrier should not substantially interact with the agent so that the agent may perform its function as described herein. Generally, the carrier will represent from about 95 percent to about 99 percent of the composition.

Preferably the carrier will comprise an alcohol. Alternatively, the carrier may be liposomes or hydrated lipidic lamellar phases, such as are well-known to those of ordinary skill in the art when said carrier is effective in functioning in accordance with the invention as contemplated herein.

Preferred formulations of the carrier contain an alcohol (e.g., methanol, ethanol or isopropanol), and a thickener such as propylene glycol, polyethylene glycol (PEG) or carbopol and a penetration enhancer such as transcutol. The total composition will comprise from about $10^{-6}\%$ to 1.0% of an effective prostaglandin. More preferably from $10^{-4}$ to 0.1% prostaglandin.

Specific examples of preferred carrier formulations into which the prostaglandin is disposed are:

(1) 30% propylene glycol (PG): 70% ethanol;
(2) 30% PG: 1.0–2.5% oleic acid or oleyl alcohol: ethanol (QS);
(3) 10–40% ethoxydiglycol: 0–2.5% oleic acid or oleyl alcohol: 0–5% hydroxypropyl cellulose: ethanol (QS);
(4) 10–50% methylpyrrolidone: 0–40% ethoxydiglycol: 0–2.5% oleic acid or oleyl alcohol: 0–5% hydroxypropyl cellulose: ethanol (QS).

The formulations described herein could be topically applied in a number of ways to achieve penetration of the prostaglandin through the skin leading to pigmentation. The composition of matter is preferably in a gel, lotion or solution form which may be manually rubbed on the skin. Other means of application are acceptable such as aerosol sprays or the use of an applicator bottle. Typically, the formulation will be applied over the skin in a dosage of 0.3 to 1 ml/100 cm$^2$. This formulation may be applied at a frequency of every one to two to six to eight to 12 hours to the areas where pigmentation is desired to achieve the desired degree of pigmentation. As defined herein the term dosage means the amount and frequency of application of the formulation to the skin. A formulation may comprise a film former such as polyvinyl pyrrolidone. Furthermore, as noted above, a penetration enhancer (such as transcutol (ethoxydiglycol)) that allows the composition to accumulate in the stratum corneum can be used.

Additional ingredients may also be included in the compositions of the present invention. Penetration enhancers, when present, will preferably comprise from about 0.5–40% weight to the solvent mixture and more preferably will comprise from 1.0–20% by weight. Transcutol is a preferred penetration enhancer, but other known enhancers such as Azone (laurocapram), calcium thioglycolate, alkanecarboxylic acids, liposomes, DMSO, polar lipids, dimethylformamide, N-methyl-2-pyrrolidone, oleic acid, oleyl alcohol, decylmethyl sulfoxide, and propylene glycol are also enabled herein and may comprise portions of the formulation. Other possible penetration enhancers which may be used in any of the compositions described herein include: lauryl alcohol, dibutyl sebacate, diethyleneglycol oleate, diethyl sebacate, diethyl succinate, diisopropyl sebacate, dioctyl adipate, dioctyl azelate, dioctyl sebacate, ethyl acetate, glycerol monolaurate, glycerol monooleate, isopropyl isostearate, isopropyl myristate, isopropyl palmitate, sucrose monolaurate, sucrose monooleate, lactic acid, lauric acid, linoleic acid, linolenic acid, vaccenic acid, EO-2-oleyl ether, EO-5-oleyl ether, EO-10-oleyl ether, N-methyl-2-pyrrolidone, pyrrolidone/carboxylic acid combinations, ethanol, polyethylene glycol, Tween 20 and Tween 80.

The composition may further comprise one or more hydrotropic substances which function to increase disorder in the lamellar liquid crystalline structure of the stratum corneum and thus allow increased transdermal transport. Examples of such hydrotropes are isopropyl alcohol, propylene glycol and sodium xylene sulfonate.

Applicants further contemplate that the formulations may comprise combinations of effective prostaglandins, and may include effective methylxanthines such as theophylline and isobutylmethylxanthine, theophylline and aminophylline, and isobutylmethylxanthine and aminophylline, or salts of derivatives of any of the above. For example, the methylxanthine component may comprise from 5 to 95% of theophylline and from 5 to 95% of IBMX, the percentages adding up to 100%. The methylxanthine component may comprise from 5 to 95% of theophylline and from 5 to 95% of aminophylline, the percentages adding up to 100%. The methylxanthine component may comprise from 5 to 95% of IBMX and from 5 to 95% of aminophylline, the percentages adding up to 100%. Further, the methylxanthine component may comprise from 5 to 95% of theophylline, from 5 to 95% of IBMX and from 5 to 95% of aminophylline, the percentages adding up to 100%.

The compositions of the present invention may further comprise other cosmetically and therapeutically acceptable carriers or vehicles containing other solvents, moisturizers, humectants, oils, emulsifiers, thickeners, thinners, surface active agents, fragrances, preservatives, antioxidants, vitamins and minerals.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Organ Culture System

Use of a human organ culture emulates the human skin in vivo and has permitted the adequate evaluation and development of the compositions and methods of treatment of the present invention. The human organ culture of the present invention employs a viable foreskin. "Viable" means there has been no substantial morphological change in the foreskin after surgical removal. Viability may be determined by changes in tissue ultrastructure determined through histochemical staining and/or dopa reaction staining, techniques which permit monitoring of any changes in the tissue ultrastructure.

The foreskins may be obtained by circumcising male neonates by standard surgical procedures. After surgical removal, the foreskin is preferably prepared for the organ culture by injection intradermally with the medium described hereafter. This swells the mucous membrane and allows for the removal of the membrane thereby allowing adequate nutrient flow to the foreskin through the dermis.

The foreskin comprises an epidermis which is normally exposed to the environment and a dermis opposing the epidermis. After surgical removal and preparation for the organ culture, the dermis, which is normally supplied nutrients by the body, is exposed to the environment. In order to maintain the viability of the foreskin, a nutrient medium supplies nutrients to the foreskin through the dermis as described hereafter.

The nutrient medium is any composition which maintains the viability of the foreskin. Preferably, the nutrient medium has a liquid phase such as a solution, suspension or emulsion. A portion of the medium may be obtained commercially, such as Iscove's modified Dulbecco's medium (IMDM), Ham's nutrient mixture F-10 medium, Minimum essential media (MEM), RPMI media 1630 or 1640, Dulbecco's Modified Eagle Media (D-MEM) or Media 199 all of which are manufactured by Gibco Laboratories of Grand Island, N.Y. as well as other companies, the specification sheets of which are hereby incorporated by reference. Additionally the medium comprises about 10% to about 30% horse serum and about 2% to about 10% fetal bovine serum; such serums may be purchased from Hyclone Lab Inc., of Logan, Utah, for example. If necessary, an alkalizer such as sodium bicarbonate may be added until the medium achieves a preferred pH, preferably about a physiological pH. Antibiotics such as penicillin and/or streptomycin may also be added for microbial control.

If transportation of the foreskin is necessary after surgical removal, the foreskin is immediately placed on an absorbent support saturated with the nutrient medium. In order to maintain the viability of the foreskin, the foreskin is disposed in the medium within about 3–4 hours after surgical removal. The position of the foreskin in the medium should be that the dermis contacts the medium and the epidermis is not substantially contacted by the medium.

Figure 2:
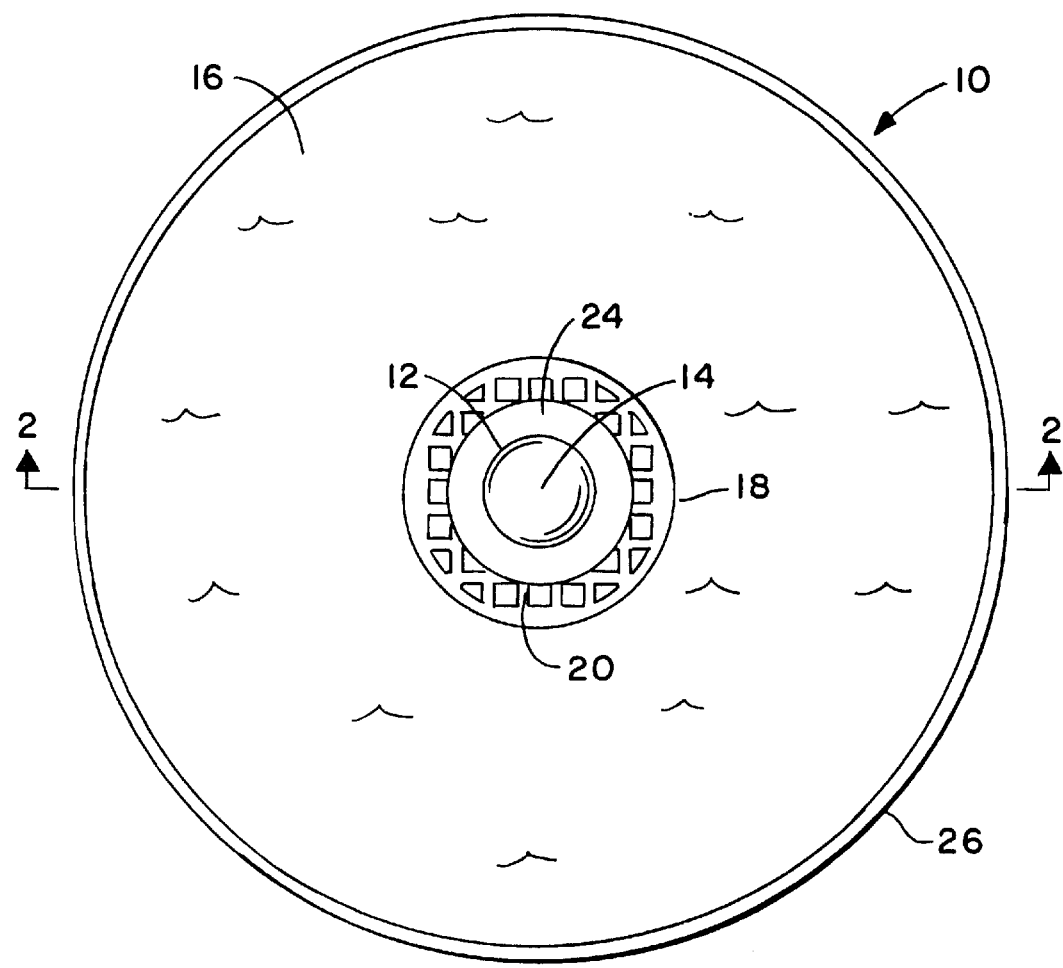
FIG. 2 is a plan view of the organ culture system used in testing the compositions of the present invention.
Figure 3:
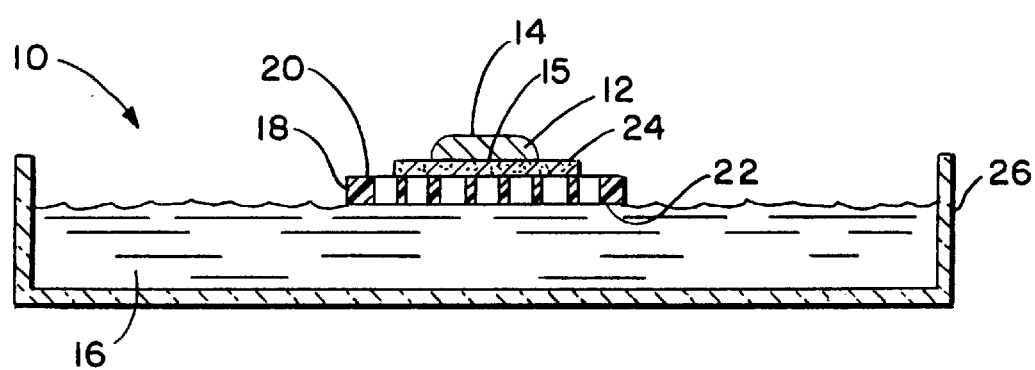
FIG. 3 is a side cross-section view of the organ culture system shown in FIG. 2 taken along line 2—2 shown in FIG. 2.

Referring to FIGS. 2 and 3, an organ culture system 10 comprises a foreskin 12 having an epidermis 14 and a dermis 15. The foreskin 12 is placed in the medium 16 so that the medium 16 contacts the dermis 15 but does not substantially contact the epidermis 14. The epidermis 14 is in contact with the environment as under in vivo conditions. The medium 16 nourishes the foreskin 12, and maintains its viability while the organ culture is under study. About 7 days or less are generally needed to complete such a study.

The medium 16 comprises a liquid phase and is disposed in a container such as a petri dish 26. The amount of medium needed will depend upon, among other things, the container and the support means used. Generally about 5 ml to about 10 ml is a sufficient amount of medium for one foreskin in a petri dish having a diameter of 1.5 inches with the foreskin supported on a float as described hereafter.

The foreskin 12 may be supported by any means which will permit positioning of the foreskin in the medium 16 as previously described. Preferably, the foreskin 12 is disposed on a buoyant and permeable float 18 having a top 20 and a bottom 22; the dermis 15 contacts the top 20 of the float 18. The float 18 floats on top of the medium 16. The float 18 preferably comprises a sterile plastic screen such as a Swinnex 25 cm filter support screen manufactured by Millipore. More preferably, a permeable pad 24 is interposed between the dermis 15 and the top 20 of the float 18. The pad 24 functions to hold the foreskin 12 on the float 18. One example of a pad 24 used in accordance with the present invention is a AP20 025 00 filter manufactured by Millipore. Because both the float 18 and pad 24 are permeable to the culture medium 16, the medium maintains contact with the dermis 15 while the foreskin is positioned on the float 18, as required to maintain the foreskins viability. The float 18 is placed on top of the medium 16 and may freely move about the top of the medium 16.

Once the foreskin is disposed in the organ culture system as described herein, the organ culture system is incubated during the length of observation of the foreskin. Preferably the medium is changed daily, since nutrients may be depleted over time, and the incubation causes degradation of medium components.

In preparing the human organ culture system described herein, the foreskin is surgically removed, prepared and disposed in the organ culture system as described herein. Before positioning the foreskin in the system, the foreskin should be observed to determine the amount and/or the condition of the biological factor under study to obtain a baseline measurement. After treatment of the foreskin with an agent, the biological factor is again observed for a post-treatment measurement to be compared to the baseline measurement. For example, if the amount of tyrosinase in the foreskin is under study, the amount of tyrosinase is determined as a baseline measurement prior to application of the agent to the foreskin.

If the foreskin is to be treated with an agent under study, the agent can be added to the medium 16 so that it comes into contact with the foreskin 12 through the medium 16. Alternatively, the agent can be placed directly upon the epidermis 14. The treatment time will depend on the results sought, the identity of the agent under study, the time over which the foreskin can remain viable, and other variables.

After the foreskin has been treated with the agent under study, the foreskin may be observed and/or tested in any manner which will determine the differences in the foreskin from the observation and/or tests on the untreated foreskin. For example, the activity of tyrosinase may be measured as described herein and correlated to an increase in melanogenesis; the rate of DNA synthesis can be measured by $^3$H-thymidine uptake and compared to controls; or the increase or decrease in the synthesis of proteins and/or RNA can be measured by determining the rate of incorporation of [$^3$H] leucine (protein) or [$^3$H] uridine (RNA) into acid-precipitating material.

Preparation of Human Foreskin and Organ Culture

At the time of surgical removal, human foreskins were placed on sterile gauze saturated with sterile IMDM medium (Iscove's modified Dulbecco's medium purchased from Irvine Scientific of Santa Ana, Calif.) for transportation from the Hospital nursery to the laboratory. The tissues were rinsed in sterile IMDM medium containing 500 U/ml penicillin and 500 µg/ml of streptomycin for 5 minutes. Under sterile conditions, an intradermal injection of medium was performed from the dermal side prior to dissection of the mucous membrane and lower dermis by scissors to make the thickness of skins equal. The foreskins were then cut into approximately 3 mm×3 mm squares and either frozen at −75° C. or placed in organ culture as described below.

The organ culture medium was prepared from IMDM with glutamine supplemented with 20% horse serum, 5% fetal bovine serum, 100 U/ml penicillin, 100 µg/ml streptomycin and 3 mg/ml sodium bicarbonate. The serums were obtained from Hyclone Lab. Inc. of Logan Utah. Culture units were prepared by placing sterilized filters (AP20 025 00, Millipore) over sterilized support screens (25 cm Swinnex filter support screens, Millipore) in the wells of 6-well tissue culture plates (Falcon 3046) with medium added to the wells such that the skin support screens floated and the filter absorbed the medium from beneath. The tissue samples were placed, epidermis up, on top of the saturated filters and incubated at 37° C. in a 5% $CO_2$ humidified atmosphere. The medium was changed everyday. Harvested cultures were frozen at −75° C. For histological study, thawed samples of fresh tissue and explants were mounted in OCT compound (ICN Immuno Biologicals, Lisle, Ill.) and frozen by liquid nitrogen. Cryostat sections (6 µm thick) were fixed in 2% formaldehyde for 2 hours at 40° C., and then stained either with hematoxylin and eosin or subjected to dopa staining. The dopa reactions were carried out by incubation in two changes of 0.1% L-dopa solution buffered to pH 7.4 in 0.1M sodium phosphate buffer for 4 hours at 37° C.

Determination of Tyrosinase Activity

Tyrosinase activity in human skin organ cultures was determined by measuring the tyrosine hydroxylase activity of the enzyme. The assay measures the production of $^3H_2O$ during the conversion of [$^3$H]tyrosine to L-DOPA. Weighed skin preparations were incubated in 0.3 ml of a reaction mixture containing 0.01 mM of L-tyrosine, 5–6 uCi/ml of [$^3$H]tyrosine and 0.1 mM L-DOPA in 0.1M of pH 6.8 phosphate buffer for 4 hours at 37° C. To terminate the reaction, 1 ml of phosphate buffer was added, the tubes vortexed, and 0.4 ml aliquots removed in triplicate and mixed with an equal volume of Norit SG activated charcoal (10% w/v, in 0.1N HCl). Following centrifugation at 2000×g for 10 min, the supernatants (0.5 ml) were placed in scintillation vials, scintillation fluid added, and vials counted in a TM Analytic 6895 scintillation counter equipped with a DPM processor.

Evaluation of Foreskin Treatment

Figure 4:
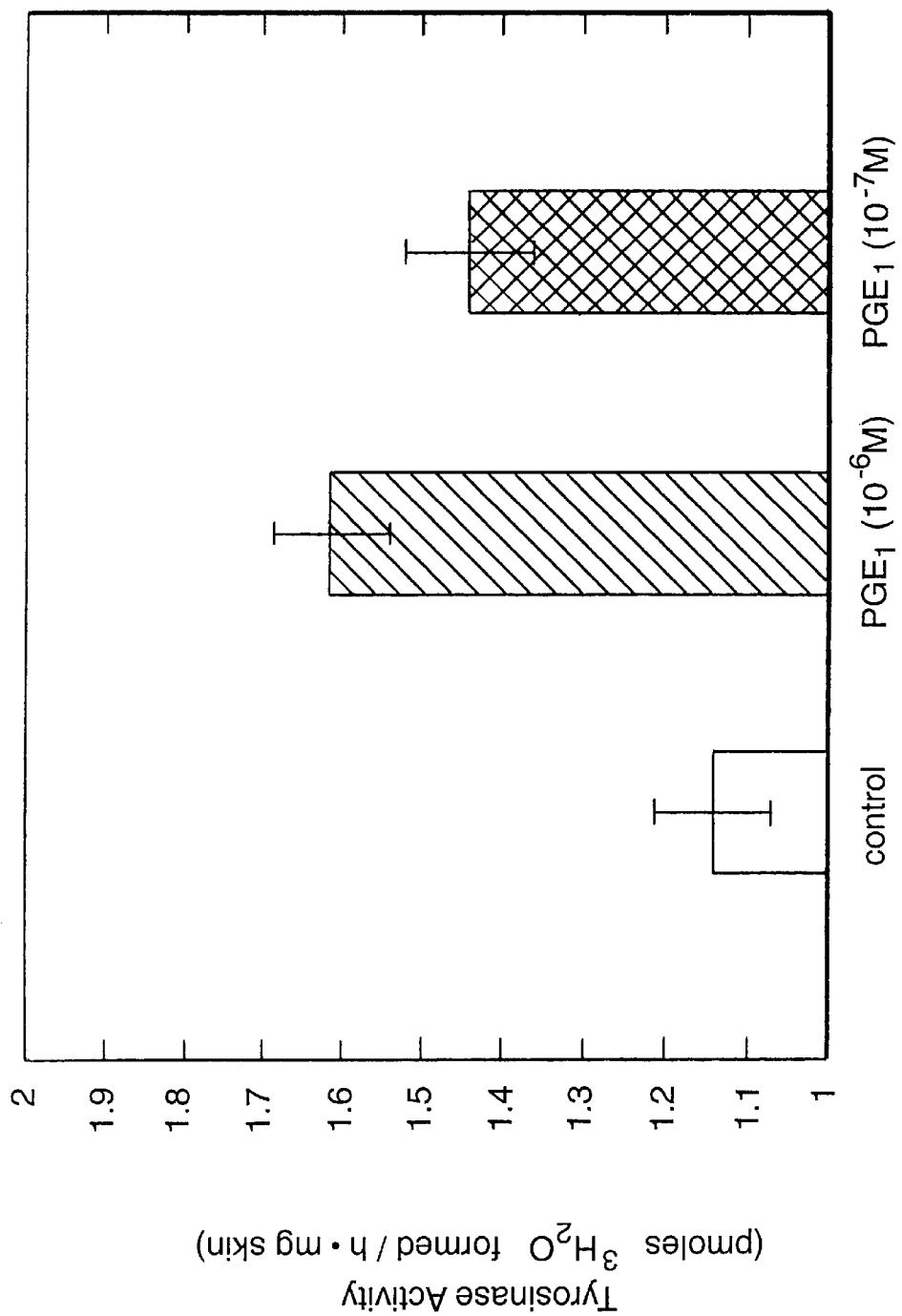
FIG. 4 is a graph showing the effect of prostaglandin $E_1$ on tyrosinase activity in human skin culture.

Table III shows the activity of prostaglandin $E_1$ in a pharmaceutical topical carrier. Organ cultures were incubated with the compounds shown in Table III for 72 hours. The medium and compounds were changed daily. Tyrosinase activity was determined by measuring the tyrosine hydroxylase activity of the enzyme. Skin treated with 1 µM $PGE_1$ ($10^{-6}$M) showed a 1.4 fold increase in tyrosinase activity over the control. Skin treated with 0.1 µM $PGE_1$ ($10^{-7}$M) showed an increase of 1.26 fold. These results are also presented in FIG. 4.

TABLE III

Effect of $PGE_1$ (Prostaglandin $E_1$) in vehicle[a]
on tyrosinase activity in human foreskin organ cultures

| Treatment | Tyrosinase Activity pmoles $^3H_2O$/hour/mg skin |
|---|---|
| control | 1.14 ± 0.070 |
| $PGE_1$ ($10^{-6}$M) | 1.616 ± 0.064 |
| $PGE_1$ ($10^{-7}$M) | 1.441 ± 0.084 |

[a]vehicle consists of 20% water, 50% isopropanol and 30% glycerol.
Values are the averages of triplicate assays ± s.d.

Melanocyte Bioassay

The normal human melanocyte cell strains used in this study were derived from foreskins of either neonates or from 2–6 year old males. Human melanocyte cultures were grown in Ham's F-10 nutrient medium supplemented with 10% horse serum, 5% fetal bovine serum (FBS), 32 nM TPA (12-O-tetradecanoylphorbol 13-acetate), penicillin (100 units/ml), and streptomycin (100 µg/ml).

To determine tyrosinase activity in situ in human melanocyte cultures, the tyrosine hydroxylase activity of the enzyme was determined. Cells were seeded into 60-mm culture dishes at $2 \times 10^5$ cells/dish and allowed to attach overnight. The medium was then exchanged with a growth medium comprising Ham's F-10 nutrient medium +10% FBS+2 µg/ml Bovine Pituitary Extract (BPE) +2 ng/ml of Fibroblast growth factor (FGF), supplemented with 1 µCi/ml of [$^3$H]tyrosine (L-ring-3,5-$^3$H]-tyrosine, DuPont New England Nuclear), and with prostaglandin, where indicated. Cells were grown in labeled medium for 24 hours, and at this time, the medium was removed and assayed for the presence of $^3H_2O$ using the charcoal absorption method of Pomerantz. Tyrosinase activity in cell homogenates was determined by sonicating cell pellets in 0.1-M sodium phosphate buffer (pH 6.8) and then incubating 50-µl aliquots in 0.5 ml of a reaction mixture containing 0.1-mM tyrosine, 2 µCi/ml of [$^3$H]tyrosine, 0.1-mM L-DOPA (dihydroxyphenylalanine), and 0.1 mM PMSF (phenylmethylsulfonyl fluoride) at 37° C. for 2 hours. Reactions were terminated by the addition of 1 ml of charcoal (10% w/v in 0.1-N HCl). Samples were centrifuged, and the supernatants removed for determination of the amount of $^3H_2O$ produced.

The amount of melanin in melanocytes was determined by incubating cell pellets in 2 ml of 1-N NaOH for 48 hours at 37° C. and then measuring the solubilized melanin at 400 nm.

Results

Figure 5:
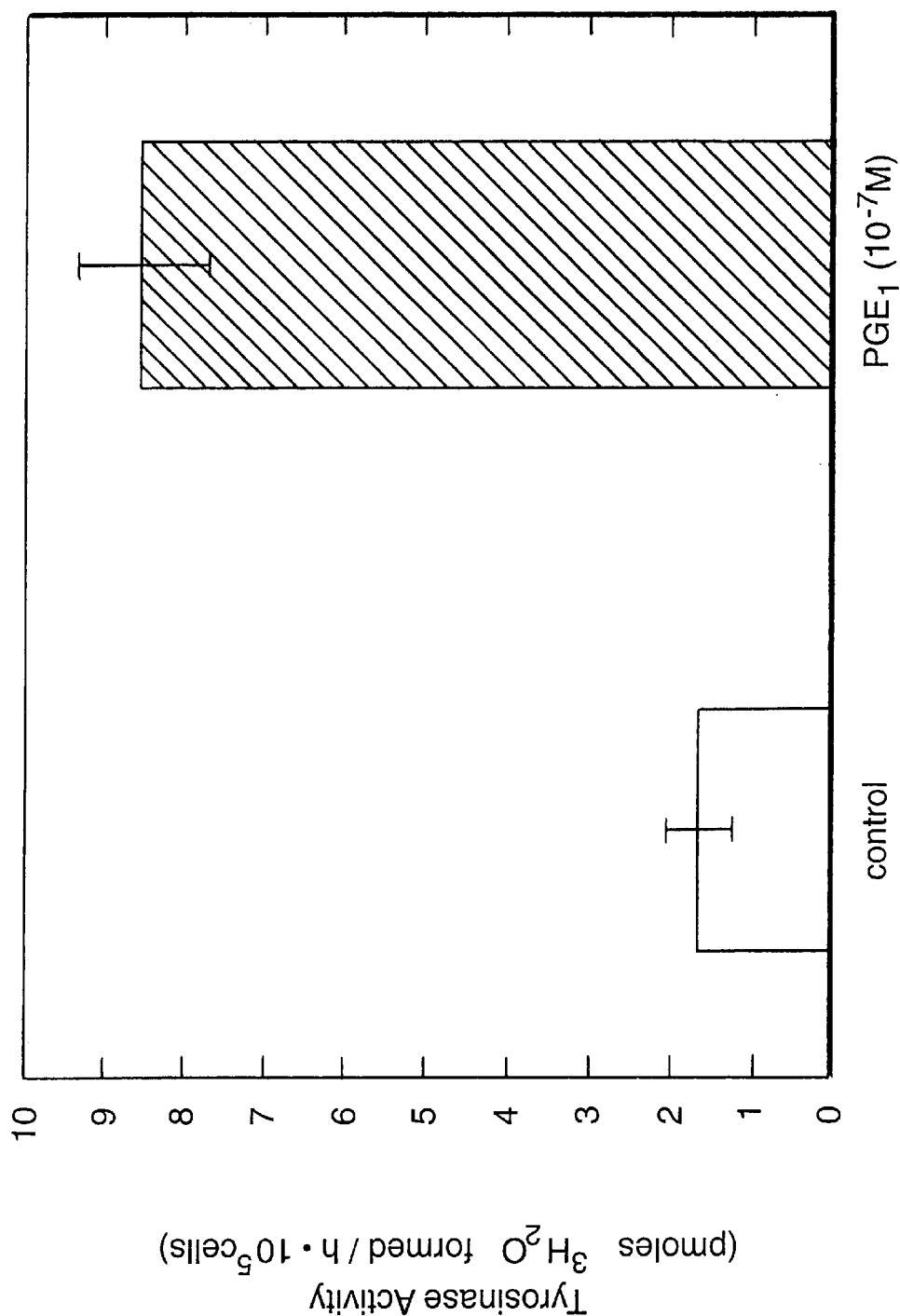
FIG. 5 is a graph showing the effect of prostaglandin $E_1$ on tyrosinase activity in human melanocyte cell culture.
Figure 6:
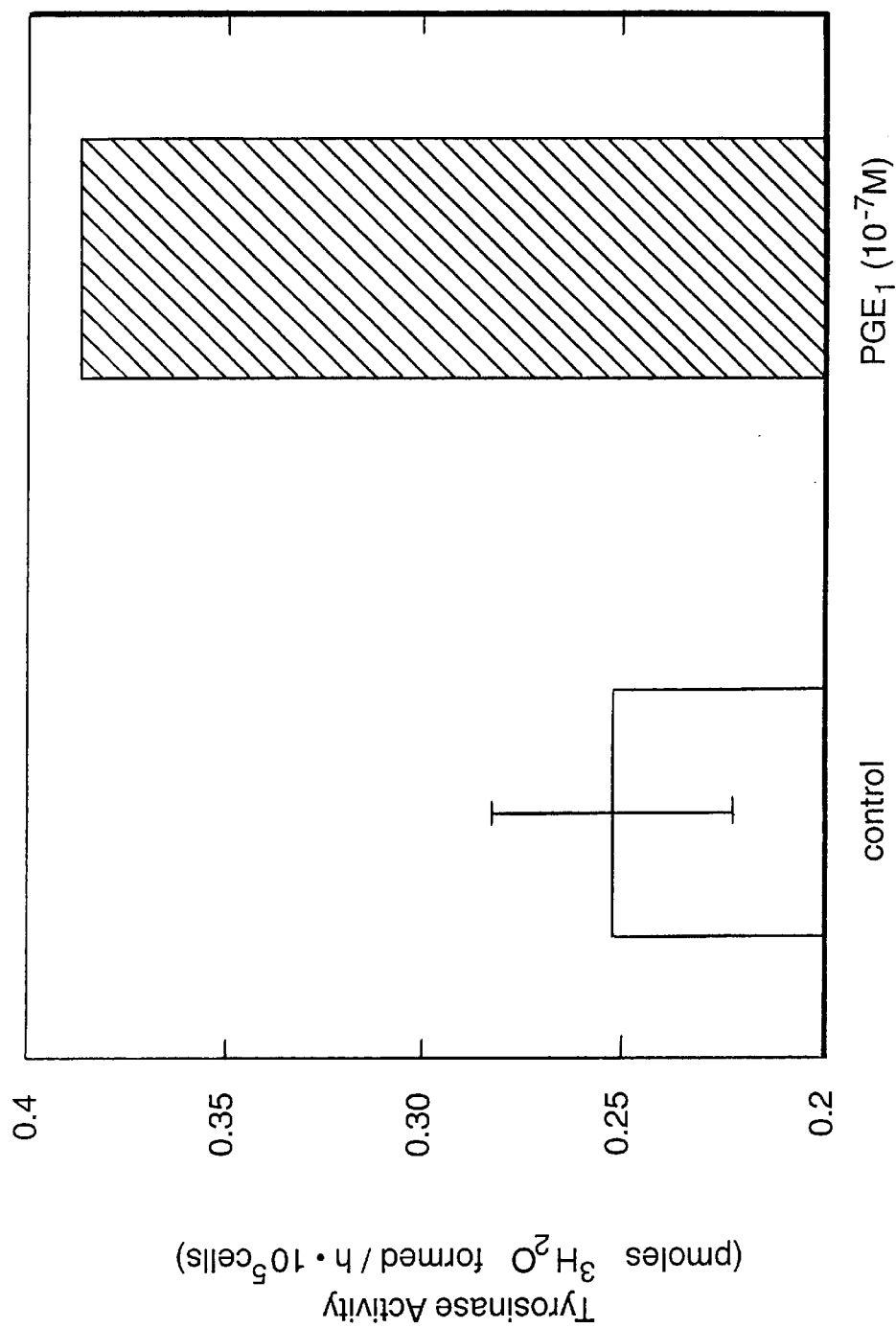
FIG. 6 is a graph showing the effect of prostaglandin $E_1$ on tyrosinase activity in another human melanocyte cell culture.

The effects of prostaglandin $E_1$, at a concentration of $10^{-7}M$, in separate experiments are shown in FIGS. 5 and 6. Cells from the 69W human melanocyte cell strain were prepared as described above. The tyrosinase activity in cell cultures treated with $PGE_1$ was over five fold greater than that seen in the control (FIG. 5). In cultures prepared from the 93-A2 cell strain, tyrosinase activity in cell cultures treated with $PGE_1$ was 1.5 fold greater than that seen in the control (FIG. 6).

Figure 7:
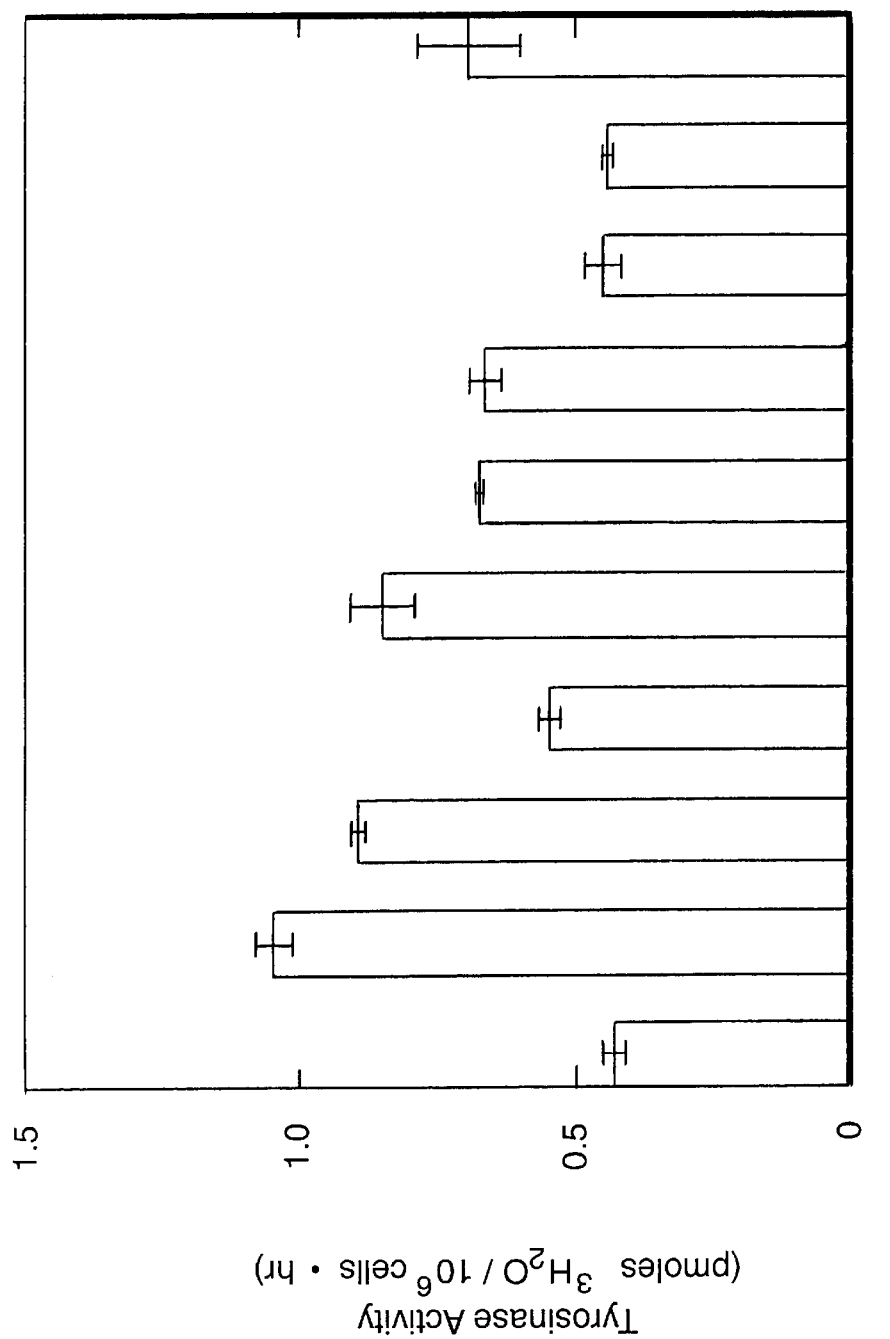
FIG. 7 is a graph showing the effect of several types of prostaglandins on tyrosinase activity in another human melanocyte cell culture.

The effects of other prostaglandins are shown in FIG. 7. Cells from the W425 cell strain were analyzed 72 hours after stimulation by TPA media. Prostaglandins $E_2$, 6-Keto $E_1$ and 13,14-dihydro $E_1$ stimulated tyrosinase activity approximately two-fold over the control. Prostaglandins $A_1$, $A_2$ and $H_2$ stimulated tyrosinase activity approximately 1.5 fold over the control. Prostaglandins 6-keto $F_{1\alpha}$, $B_1$ and $B_2$ had zero to little stimulatory effect on tyrosinase activity. In separate experiments, prostaglandins $D_2$, $F_2$, $F_{2\alpha}$ were also ineffective in stimulating tyrosinase activity. In later work, $PG-B_2$ was effective when supplied at higher concentrations $(10^{-6}M)$.

Figure 8:
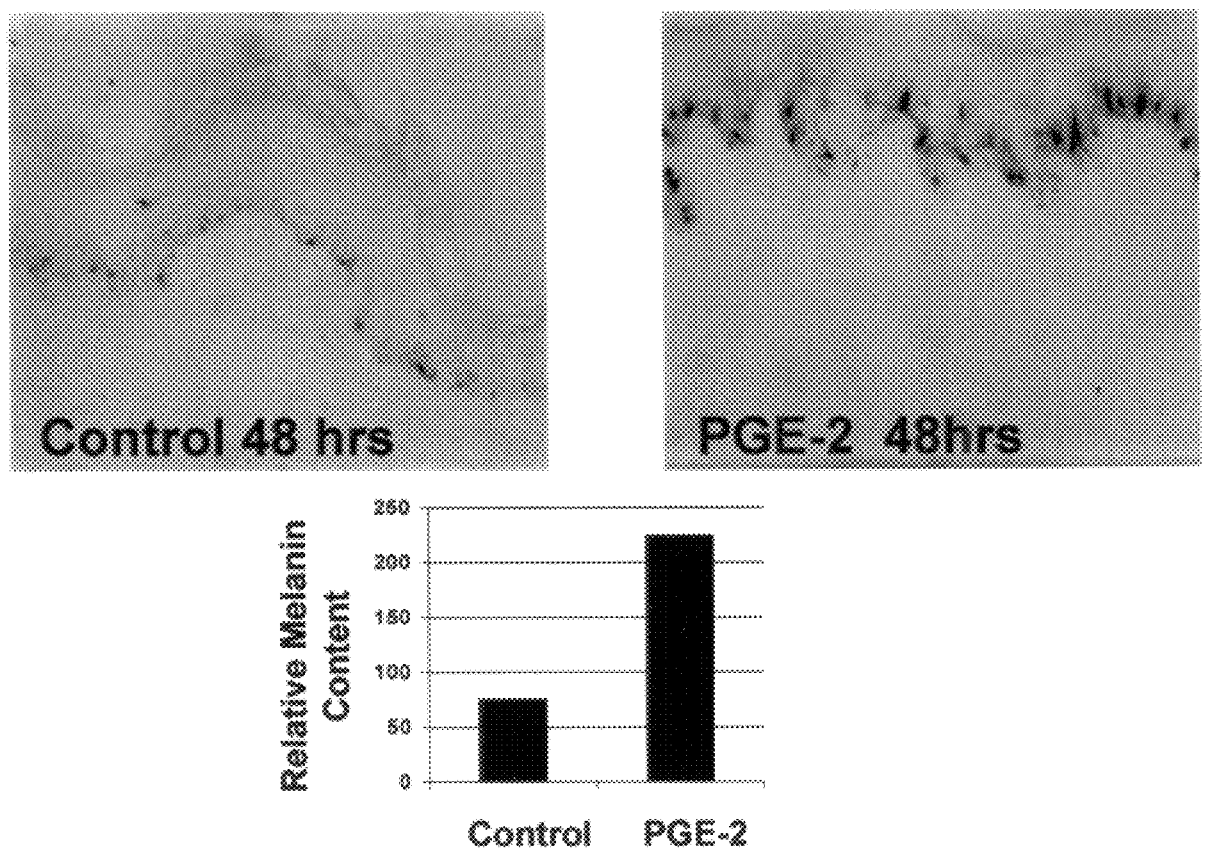
FIG. 8 are sectional micrographs through organ cultures treated with $PGE_2$ and with vehicle only.

FIG. 8 shows sections taken through organ cultures incubated for 48 hours, treated with $PGE_2$ in a vehicle or only with the vehicle (control). After 48 hours, the tissues treated with $PGE_2$ had three times the melanin content as the tissue treated only with the carrier vehicle.

Figure 9:
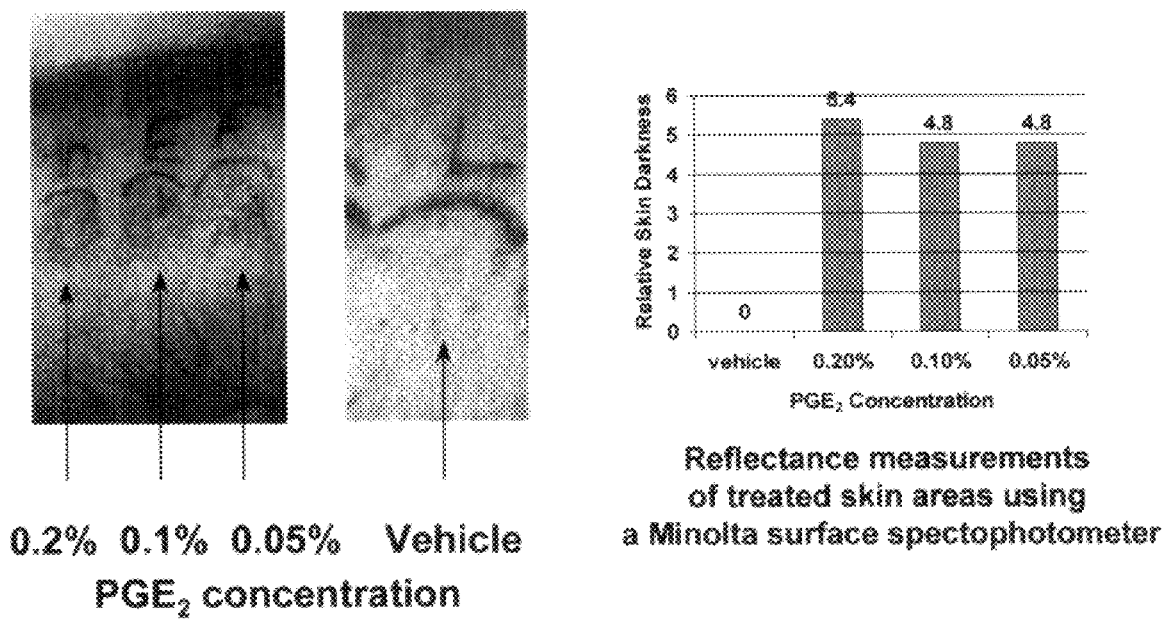
FIG. 9 is a photograph and graph showing the stimulation of pigmentation by prostaglandin $E_2$ in the skin of a living pig.

Finally, FIG. 9 is a pair of photographs and a graph representing the results of several concentrations of $PGE_2$ applied to the shaved skin of a living Yucatan pig. Three concentrations of $PGE_2$ in the carrier (0.2%, 0.1% and 0.05% $PGE_2$) were applied to shaved skin of the pig for seven days, three times per day. As shown in the photographs, and in the graph, the vehicle alone stimulated no darkening of the skin, while all three of the levels of $PGE_2$ which were tested caused darkening of the skin as measured by reflectance of the treated skin areas. The vehicle used in the pig skin studies comprised 25% transcutol, 1% oleic acid, 2% hydroxy propyl cellulose, prostaglandin (from 0.05% to 0.2%), and ethanol to make up 100%.

These data show that prostaglandins having a 9-keto group (particularly those having a saturated cyclopentane ring), or a 9,11 epidoxy group, or 9β,11α hydroxy groups were effective in stimulating tyrosinase activity, and that prostaglandins not having these features were ineffective, or had very little effect, in stimulating tyrosinase activity in human melanocyte cells. 9-keto prostaglandins having a $C_{10}$–$C_{11}$ double bond ($A_1$ and $A_2$) were slightly less effective than 9-keto prostaglandins having a saturated cyclopentane ring. Prostaglandin $H_2$ has an epidoxy group attached at the 9 and 11 positions of the cyclopentane ring and, is also contemplated as an effective prostaglandin, as are prostaglandins having together α, and β first and second side chains and 9β,11α hydroxy groups.

Changes may be made in the various compositions and methods of use described herein or in the steps or the sequence of steps of the methods described herein without departing from the spirit and scope of the invention as defined in the following claims.

What is claimed is:

1. A method for stimulating melanogenesis in human skin in vivo, comprising:
    applying to the skin a composition comprising:
        an effective amount of a prostaglandin or salt thereof which is able to increase levels of melanin in a human melanocyte; and
        an effective amount of a pharmaceutically acceptable carrier capable of delivering the effective amount of the prostaglandin to the melanocyte in the skin.

2. The method of claim 1 wherein in the step of providing the composition, the prostaglandin has a concentration of 0.01 μM to about 10 mM in the composition.

3. The method of claim 1 wherein in the step of providing the composition, the prostaglandin comprises from about $10^{-4}$% to about 1% by weight of the composition.

4. The method of claim 1 wherein in the step of providing the composition, the prostaglandin comprises from about $10^{-4}$% to about 0.1% by weight of the composition.

5. The method of claim 1 wherein in the step of providing the composition, the prostaglandin comprises from about $10^{-3}$% to about 0.1% by weight of the composition.

6. The method of claim 1 wherein the prostaglandin comprises at least one of: $PGA_1$; $PGA_2$; $PGB_2$; $PGE_1$; $PGE_2$; $PGH_2$; 6-keto $PGE_1$; 13,14-dihydro $PGE_1$; Misoprostol; 11-deoxy $PGE_1$; 8-iso $PGE_1$; 11-β $PGE_1$; 15(R)-$PGE_1$; 15-keto $PGE_1$; 13,14-dihydro-15(R) $PGE_1$; 13,14-dihydro-15-keto $PGE_1$; 16,16-dimethyl-6-keto $PGE_1$; 19(R)-hydroxy $PGE_1$; 16,16-dimethyl $PGA_1$; 13,14-dihydro-15-keto $PGA_2$; 16,16-dimethyl $A_2$; 17-phenyl trinor-13,14-dihydro $PGA_2$; 8-iso $PGE_2$; 15-keto $PGE_2$; 16,16-dimethyl $PGE_2$; 11β-$PGE_2$; 13,14-dihydro-15-keto $PGE_2$; 15(R)-$PGE_2$; $PGE_2$ methyl ester; Sulprostone; 17-phenyltrinor $PGE_2$; 19(R)-hydroxy $PGE_2$; 20-hydroxy $PGE_2$; $PGF_{1\beta}$; $PGF_{2\beta}$, 5-trans $PGF_{2\beta}$; and tromethamine salts of the above.

7. The method of claim 1 wherein in the step of providing the composition, the composition further comprises a methylxanthine selected from the group consisting of theophylline, isobutyl methylxanthine, aminophylline and pharmaceutically acceptable salts of theophylline, isobutyl methylxanthine or aminophylline capable of increasing melanin in the human melanocyte and wherein the pharmaceutically acceptable topical carrier is capable of delivering the methylxanthine to the melanocyte under in vivo conditions.

8. The method of claim 7 wherein in the step of providing the composition, the methylxanthine has a concentration of from about 0.01 mM to about 1M in the composition.

9. The method of claim 1 wherein in the step of providing the composition, the composition further comprises an amount of dibutyryl cAMP effective in stimulating melanin production.

10. The method of claim 1 wherein in the step of providing the composition, the composition further comprises a lysosomotropic agent.

11. A method for stimulating melanogenesis in human skin in vivo, comprising:
    applying to the skin a composition comprising:
        an effective amount of a prostaglandin or salt thereof which is able to increase levels of melanin in a human melanocyte, the prostaglandin or salt, thereof having a cyclopentane ring having positions 8–12, a side chain bonded to the 8 position in an α configuration, and a side chain bonded to the 12 position in a β configuration, the cyclopentane ring further comprising:
            a carbonyl oxygen in the 9 position,
            an epidoxy group in the 9, 11 position, or
            a first hydroxyl group bonded to the 9 position in a β configuration and a second hydroxyl group bonded to the 11 position in an α configuration; and
        an effective amount of a pharmaceutically acceptable carrier capable of delivering the prostaglandin to the melanocyte in the skin.

12. The method of claim 11 wherein in the step of providing the composition, the prostaglandin has a concentration of 0.01 μM to about 10 mM in the composition.

13. The method of claim 11 wherein in the step of providing the composition, the prostaglandin comprises from about $10^{-4}$% to about 1% by weight of the composition.

14. The method of claim 11 wherein in the step of providing the composition, the prostaglandin comprises from about $10^{-4}$% to about 0.1% by weight of the composition.

15. The method of claim 11 wherein in the step of providing the composition, the prostaglandin comprises from about $10^{-3}$% to about 0.1% by weight of the composition.

16. The method of claim 11 wherein the prostaglandin comprises at least one of: $PGA_1$; $PGA_2$; $PGB_2$; $PGE_1$; $PGE_2$; $PGH_2$; 6-keto $PGE_1$; 13,14-dihydro $PGE_1$; Misoprostol; 11-deoxy $PGE_1$; 8-iso $PGE_1$; 11-β $PGE_1$; 15(R)-$PGE_1$; 15-keto $PGE_1$; 13,14-dihydro-15(R) $PGE_1$; 13,14-dihydro-15-keto $PGE_1$; 16,16-dimethyl-6-keto $PGE_1$; 19(R)-hydroxy $PGE_1$; 16,16-dimethyl $PGA_1$; 13,14-dihydro-15-keto $PGA_2$; 16,16-dimethyl $A_2$; 17-phenyl trinor-13,14-dihydro $PGA_2$; 8-iso $PGE_2$; 15-keto $PGE_2$; 16,16-dimethyl $PGE_2$; 11-$PGE_2$; 13,14-dihydro-15-keto $PGE_2$; 15(R)-$PGE_2$; $PGE_2$ methyl ester; Sulprostone; 17-phenyltrinor $PGE_2$; 19(R)-hydroxy $PGE_2$; 20-hydroxy $PGE_2$; $PGF_{1\beta}$; $PGF_{2\beta}$; 5-trans $PGF_{2\beta}$; and tromethamine salts of the above.

17. The method of claim 11 wherein in the step of providing the composition, the composition further comprises a methylxanthine selected from the group consisting of theophylline, isobutyl methylxanthine, aminophylline and pharmaceutically acceptable salts of theophylline, isobutyl methylxanthine or aminophylline capable of increasing melanin in the human melanocyte and wherein the pharmaceutically acceptable topical carrier is capable of delivering the methylxanthine to the melanocyte under in vivo conditions.

18. The method of claim 17 wherein in the step of providing the composition, the methylxanthine has a concentration of from about 0.01 mM to about 1M in the composition.

19. The method of claim 11 wherein in the step of providing the composition, the composition further comprises an amount of dibutyryl cAMP effective in stimulating melanin production.

20. The method of claim 11 wherein in the step of providing the composition, the composition further comprises a lysosomotropic agent.

21. A method for stimulating melanogenesis in human skin in vivo, comprising:
applying to the skin a composition comprising:
an effective amount of a prostaglandin capable of increasing levels of melanin in a human melanocyte, the prostaglandin of the general formula I,

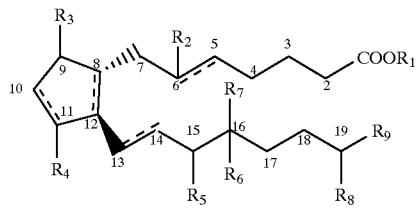

(I)

in which
$R_1$ is a hydrogen atom, an alkyl group, a sulfonyl group or a derivative thereof, or a tromethamine group, $R_2$ is a hydrogen atom, or a carbonyl oxygen atom when the $C_5$–$C_6$ bond is single or is absent when the $C_5$–$C_6$ bond is double, $R_3$ is a carbonyl oxygen atom, an oxygen atom bonded to another oxygen atom in the 11 position, or a β-hydroxyl group, $R_4$ is a hydrogen or hydroxyl group when the $C_{10}$–$C_{11}$ bond is a single bond, is absent when the $C_{10}$–$C_{11}$ bond is a double bond, is an oxygen atom bonded to an oxygen atom in the 9 position, or is an α-hydroxyl group when $R_3$ is a β-hydroxyl group, $R_5$ is a hydrogen atom, a hydroxyl group, a carbonyl oxygen, or a hydroxyl and methyl pair, $R_6$ is a hydrogen atom or a methyl group, $R_7$ is a hydrogen atom or a methyl group, $R_8$ is a hydrogen atom or a hydroxyl group, and $R_9$ is a hydroxyl group or an alkyl group; and an effective amount of a pharmaceutically acceptable topical carrier capable of delivering the effective amount of the prostaglandin to the melanocyte in the skin.

22. The method of claim 21 wherein in the step of providing the composition, the prostaglandin has a concentration of 0.01 μM to about 10 mM in the composition.

23. The method of claim 21 wherein in the step of providing the composition, the prostaglandin comprises from about $10^{-4}$% to about 1% by weight of the composition.

24. The method of claim 21 wherein in the step of providing the composition, the prostaglandin comprises from about $10^{-4}$% to about 0.1% by weight of the composition.

25. The method of claim 21 wherein in the step of providing the composition, the prostaglandin comprises from about $10^{-3}$% to about 0.1% by weight of the composition.

26. The method of claim 21 wherein in the step of providing the composition, the composition further comprises a methylxanthine selected from the group consisting of theophylline, isobutyl methylxanthine, aminophylline and pharmaceutically acceptable salts of theophylline, isobutyl methylxanthine or aminophylline capable of increasing melanin in the human melanocyte and wherein the pharmaceutically acceptable topical carrier is capable of delivering the methylxanthine to the melanocyte under in vivo conditions.

27. The method of claim 26 wherein in the step of providing the composition, the methylxanthine has a concentration of from about 0.01 mM to about 1M in the composition.

28. The method of claim 21 wherein in the step of providing the composition, the composition further comprises an amount of dibutyryl cAMP effective in stimulating melanin production.

29. The method of claim 21 wherein in the step of providing the composition, the composition further comprises a lysosomotropic agent.

* * * * *